United States Patent
Lai et al.

(10) Patent No.: US 10,174,140 B2
(45) Date of Patent: Jan. 8, 2019

(54) NON-HALOGEN FLAME RETARDANT POLYMERS

(71) Applicant: Lubrizol Advanced Materials, Inc., Cleveland, OH (US)

(72) Inventors: John Ta-Yuan Lai, Broadview Hts., OH (US); Ti Chou, Bay Village, OH (US)

(73) Assignee: LUBRIZOL ADVANCED MATERIALS, INC., Cleveland, OH (US)

( * ) Notice: Subject to any disclaimer, the term of this patent is extended or adjusted under 35 U.S.C. 154(b) by 0 days.

(21) Appl. No.: 14/893,557

(22) PCT Filed: May 23, 2014

(86) PCT No.: PCT/US2014/039353
§ 371 (c)(1),
(2) Date: Nov. 24, 2015

(87) PCT Pub. No.: WO2014/193754
PCT Pub. Date: Dec. 4, 2014

(65) Prior Publication Data
US 2016/0115259 A1   Apr. 28, 2016

Related U.S. Application Data

(60) Provisional application No. 61/827,823, filed on May 28, 2013.

(51) Int. Cl.
| C08F 30/02 | (2006.01) |
| C07F 9/09 | (2006.01) |
| C08F 230/02 | (2006.01) |
| C09K 21/14 | (2006.01) |
| C09D 143/02 | (2006.01) |
| C08K 5/3492 | (2006.01) |
| C08L 33/08 | (2006.01) |
| C08L 43/02 | (2006.01) |
| C08L 75/02 | (2006.01) |
| C08L 75/04 | (2006.01) |
| C08L 77/00 | (2006.01) |

(52) U.S. Cl.
CPC .............. *C08F 30/02* (2013.01); *C07F 9/091* (2013.01); *C08F 230/02* (2013.01); *C08K 5/34924* (2013.01); *C08L 33/08* (2013.01); *C08L 43/02* (2013.01); *C08L 75/02* (2013.01); *C08L 75/04* (2013.01); *C08L 77/00* (2013.01); *C09D 143/02* (2013.01); *C09K 21/14* (2013.01)

(58) Field of Classification Search
None
See application file for complete search history.

(56) References Cited

U.S. PATENT DOCUMENTS

| 3,883,463 | A | 5/1975 | Jin et al. | |
| 4,072,776 | A | 2/1978 | Linke et al. | |
| 4,086,385 | A | 4/1978 | Rowland | |
| 2003/0092802 | A1 | 5/2003 | Nakacho et al. | |
| 2003/0114617 | A1* | 6/2003 | Yukawa | ................ C08F 220/18 526/274 |
| 2010/0261862 | A1* | 10/2010 | Sugiyama | .............. C09K 21/14 526/238.21 |
| 2014/0357146 | A1* | 12/2014 | Gerhardt | .............. C09D 185/02 442/153 |

FOREIGN PATENT DOCUMENTS

| EP | 2194185 | | 6/2010 |
| JP | 62-119223 | * | 5/1987 |
| JP | 6-248023 | | 9/1994 |
| JP | 7-18028 | | 1/1995 |
| JP | 8-262789 | | 10/1996 |
| JP | 2007277794 | | 10/2007 |
| JP | 2010-235830 | | 10/2010 |
| JP | 2012012734 | | 1/2012 |
| WO | 2013/066906 | | 5/2013 |
| WO | 2013066908 | | 5/2013 |

OTHER PUBLICATIONS

Machine translation of Yoshio et al. JP 62-119223, May 30, 1987, p. 1-10.*
Full translation of JP 62119223 Yoshio et al pp. 1-17.*
European Patent Office, International Search Report for PCT/US14/039353, dated Aug. 26, 2014.
European Patent Office, Written Opinion for PCT/US14/039353, dated Aug. 26, 2014.

* cited by examiner

*Primary Examiner* — Robert T Butcher
(74) *Attorney, Agent, or Firm* — Christopher Demas; Teresan Gilbert

(57) ABSTRACT

Non-halogenated monomers that can be polymerized into flame retardant polymers, and processes to produce the monomers and polymers is provided. In a simplest aspect, there is provided a monomer composition that can comprise a) a group derived from one of a (meth)acrylic acid, (meth) acrylamide, or vinylbenzene, b) a polyphosphate moiety, and c) an amine species. In the monomer composition, the ethylenically unsaturated monomer of (a) is covalently bonded directly or through a linking group to the moiety of b), forming a precursor monomer unit. The amine species of c) is in complex with the precursor monomer unit. The polymer can be a homopolymer of the monomer composition, or a copolymer of the monomer composition having varying a), b) and c). In one embodiment, the polymer can additionally comprise ethylenically unsaturated monomers not covalently bonded to a polyphosphate moiety and/or can be cross-linked with a cross-linking agent such as resorcinol.

17 Claims, 1 Drawing Sheet

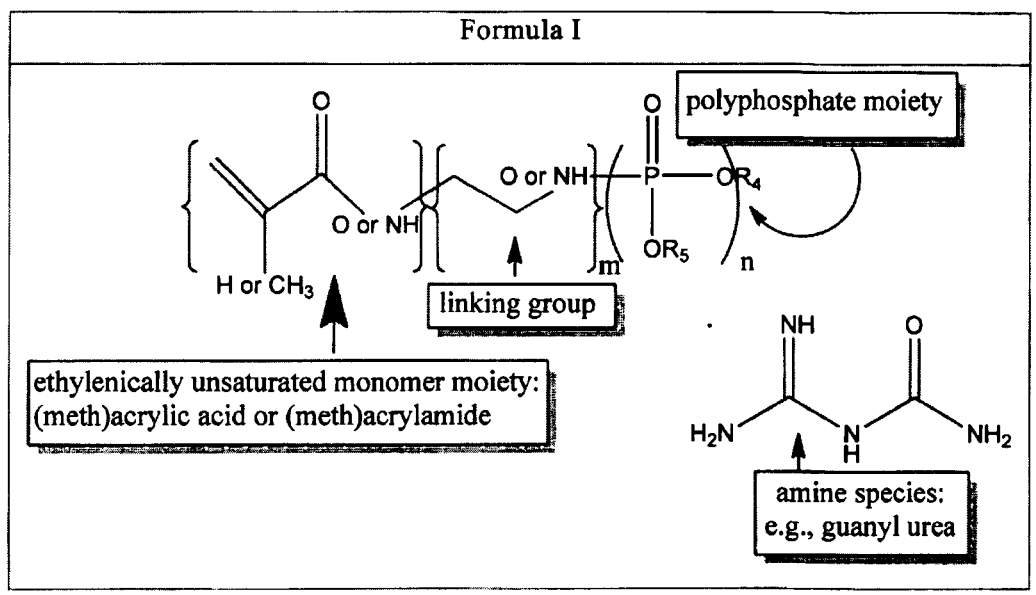

NON-HALOGEN FLAME RETARDANT POLYMERS

BACKGROUND OF THE INVENTION

The disclosed technology relates to non-halogen flame retardant compositions comprising phosphorus in complex with nitrogen, and cross-linked by a cross-linking agent, such as resorcinol.

Halogens, i.e., fluorine, chloride, bromine and iodine, can be used in fire retardant compositions. However, organic compounds containing halogens can generate toxic substances, such as dioxin and difuran, upon combustion. Organohalogens may also accumulate in the human body for long periods of time and cause hormone problems. In addition, fluorine, chloride and bromine in particular, have been known to cause severe depletion of ozone. For this reason, the use of halogens, whether as flame retardants or in other applications, is increasingly regulated. Accordingly, there is a need for non-halogenated flame retardants.

One method of obtaining a flame retardant composition is to include phosphorus in the composition. For example, U.S. Pat. No. 5,281,239 to Chatelin et al., issued Jan. 25, 1994, teaches a method of grafting a fibrous material with phosphoric acid ethylenic esters of the general formula:

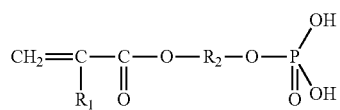

the graft rate of the ester is taught to be less than or equal to 20%.

Similarly, U.S. Publication No. 2010/0261862 to Sugiyama et al., published Oct. 14, 2010, teaches a method for grafting phosphorus containing compounds along with an amine compound onto a cellulosic fiber. The method relies on irradiating the fiber to create radicals to which the phosphorus containing compound may bind.

JP2007182652A to Toshio, published Jul. 19, 2007, teaches flame retardant additives comprising a mixture of an organic phosphorus-base-flame-retarder and a nitrogen type flame retardant. Similarly, CN 102071032 teaches the use in combination of phosphorus containing and nitrogen containing flame retardants. These publications only teach compounds containing tribasic phosphoric acid and do not teach polymerizing the compounds.

Polymer compositions containing a rubber modified vinyl resin, a polyphenylene ether resin, a cyclic alkyl phosphate compound, and an aromatic phosphate ester are taught in U.S. Pat. No. 7,829,629 to Ahn et al., issued Nov. 9, 2010. Similarly, U.S. Publication No. 2007/0192966 to Cottrell et al., published Aug. 23, 2007, teaches flame retardant phosphorus containing polymers comprised of between 10 and 100 wt. % of phosphorus containing monomer derived units. Neither of the aforementioned references teaches a polymer in which the monomers are in complex with an amine species. These polymers would be highly acidic and damaging to various substrates and thus, a transport concern.

A further problem exists in that some non-halogenated flame retardant polymers do not remain coated on a surface if and when the surface is contacted with water. For example, some surfaces are often contacted, or subject to be contacted with tap water. If the flame retardant coating washes off with the tap water, the surface will lose its flame retardance.

A need exists for new non-halogenated flame retardants, and particularly non-halogenated flame retardant polymers that less readily wash off with water.

SUMMARY OF THE INVENTION

The inventors have discovered novel flame retardant (FR) monomers that can be polymerized into novel non-halogenated flame retardant polymers.

Thus, in a simplest aspect of the invention, there is provided a novel flame retardant monomer composition. The novel flame retardant monomer composition can comprise a) a group derived from one of a (meth)acrylic acid, (meth) acrylamide, or vinylbenzene, b) a polyphosphate moiety, and c) an amine species. In the novel flame retardant monomer composition, an ethylenically unsaturated monomer of (a) is covalently bonded directly or through a linking group to the polyphosphate moiety of b), forming a precursor monomer unit. Further, the amine species of c) is in complex with the covalently bonded polyphosphate moiety of b) in the precursor monomer unit. In addition, the composition can be cross-linked with a cross-linking agent, such as resorcinol.

In one embodiment, the novel flame retardant monomer composition can be produced by reacting the precursor monomer unit with the amine species.

In another aspect of the invention, there is provided a flame retardant polymer. The flame retardant polymer can be a homopolymer of flame retardant monomeric units equivalent to, i.e., derived from, the novel flame retardant monomer composition, or a copolymer of monomeric units equivalent to the novel flame retardant monomer compositions having varying a), b) and c).

In one embodiment, the flame retardant polymer can additionally comprise monomeric units equivalent to ethylenically unsaturated monomers that are not covalently bonded to a polyphosphate moiety. In such an embodiment, at least 20% of the monomers in the polymer are monomeric units equivalent to the novel flame retardant monomer compositions of the simplest aspect of the invention, and from 0.1% to about 80% of the monomers in the polymer can be monomeric units equivalent to the ethylenically unsaturated monomers that are not covalently bonded to a polyphosphate moiety. Such a copolymer can be comprised of at least 1 wt. % P and have a number average molecular weight (Mn) of at least about 1000 g/mole.

In another embodiment of the invention, at least 90% of the monomers in the flame retardant polymer can comprise a combination of monomeric units equivalent to the ethylenically unsaturated monomers that are not covalently bonded to a polyphosphate moiety and monomeric units equivalent to the novel flame retardant monomer compositions of the simplest aspect of the invention.

In one aspect of the invention, a flame retardant polymer can be produced by several routes.

In one embodiment, the novel flame retardant monomer composition of the simplest aspect can be free-radically polymerized to form a flame retardant polymer.

In another embodiment, the flame retardant polymer can be produced by free radically polymerizing the precursor monomer units and subsequently reacting the polymerized product with the amine species.

In either embodiment of the process, ethylenically unsaturated monomer units that are not covalently bonded to a polyphosphate moiety can be in included in the free radical polymerization.

In a further aspect of the invention, flame retardant compositions are provided. The flame retardant composition can comprise the flame retardant polymers along with other additives. In particular, additives such as flame retardant additives and other polymers may be blended in the flame retardant compositions along with the flame retardant polymer.

Also provided is a method of improving the capacity of a non-halogen flame retardant polymer to withstand tap water washing, comprising preparing the non-halogen flame retardant polymer with a cross-linking agent.

Further, there is provided a method of maintaining flame retardance on a surface contacted or contactable with water, comprising applying to the surface a polymer composition as disclosed herein, including a cross-linking agent.

BRIEF DESCRIPTION OF DRAWINGS

FIG. 1 shows the chemical structure for Formula 1.

DETAILED DESCRIPTION OF THE INVENTION

Various preferred features and embodiments will be described below by way of non-limiting illustration.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The term "wt. %" means the number of parts by weight of ingredient per 100 parts by weight of the composition or material of which the ingredient forms a part.

As used herein, a polyphosphate moiety refers specifically to a group containing a phosphorus atom bonded to three oxygen ions (phosphonate) or a phosphorus atom bonded to four oxygen ions (phosphate). The polyphosphate moiety may contain mono-, di-, tri-, or higher phosphate, or a mono-, and/or di-phosphonate, and in particular a monophosphate, diphosphate, triphosphate or monophosphonate. Preferably the polyphosphate moiety is a mono-, di-, or tri-phosphate.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

(iii) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. As used herein, an alkyl group containing an oxygen atom is referred to as an alkoxyl group.

The term "coating" is used herein to refer to impregnation, saturation, roller, brush, spray, foam and curtain coating and similar procedures.

The expression "( )," such as "(meth)", "(alk)", or "(alkyl)," is used to indicate that the particular substituent in a chemical name is optionally present but may be absent. For example, the term "(meth)acrylate" may be used to refer to either acrylate or methacrylate.

As used herein the term "polymer" refers to the product of a polymerization reaction in which the molecules of one or more monomers are linked together to form large molecules whose molecular weight is a multiple of that of the one or more monomers. These polymers may be homopolymers or copolymers. These polymers may be linear polymers, branched polymers, cross-linked polymers, or a mixture of two or more thereof.

The term "homopolymer" is used herein to refer to a polymer resulting from the polymerization of a single monomer.

The term "copolymer" is used herein to refer to a polymer resulting from the polymerization of two or more chemically distinct monomers.

The term "linear polymer" refers to a polymer in which the molecules form long chains without branches or cross-linked structures.

The term "branched polymer" refers to a polymer in which the molecules form a main chain or polymer backbone and one or more additional relatively short chains are attached to the main chain or polymer backbone.

The term "cross-linked polymer" refers to a polymer in which the polymer molecules are linked to each other at points in their structures other than at the ends of the polymer chains.

The term "halogen-free" or "non-halogenated" polymer refers to a polymer that does not have any halogen atoms attached to it. In one embodiment, the halogen-free polymer is a chlorine-free polymer. The term "halogen-free" does not exclude halogen that may be present at contaminate levels, for example, levels of up to about 5% by weight, and in one embodiment up to about 2% by weight, and in one embodiment up to about 1% by weight, and in one embodiment up to about 0.5% by weight, and in one embodiment up to about 0.2% by weight, and in one embodiment up to about 0.1% by weight.

It is recognized that when a monomer is polymerized, the resultant monomeric unit within the polymer will have a structure that is slightly altered from the starting monomer. The monomeric unit is equivalent to, i.e., derived or derivable from, the starting monomer, having the same atoms in the same relative positions to each other as in the monomer, only the carbon to carbon double bond of the monomer is converted to a carbon to carbon single bond in the monomeric unit and the excess electrons from that conversion of the monomer are used to bond each monomeric unit to adjacent carbon atoms on an adjacent repeating unit of the polymer. It is to be appreciated that reference herein to a polymer comprising a monomer means that the polymer is comprised of monomeric units equivalent to, i.e., derived or derivable from, the monomer.

In a simplest aspect of the invention, there is provided a novel flame retardant monomer composition. The novel flame retardant monomer composition can comprise a) an ethylenically unsaturated monomer, such as, for example, a group derived from one of a (meth)acrylic acid, (meth)acrylamide, or vinylbenzene, b) a polyphosphate moiety, and c) an amine species. As used herein, vinylbenzene can be styrene or an alkyl substituted vinylbenzene, such as, for example, α-methyl styrene, 1-methyl-2-vinylbenzene, 1-methyl-3-vinylbenzene, 1-methyl-4-vinylbenzene and the like.

As the ethylenically unsaturated monomer, there is also contemplated, for example, 2-hydroxyethyl (meth)acrylate (HEMA). Alternatively, other monomers such as hydroxypropyl (meth)acrylate or 4-hydroxybutyl (meth)acrylate are contemplated. Likewise, 2-hydroxyethyl (meth)acrylamide, hydroxypropyl (meth)acrylamide, polyethyleneglycol (meth)acrylate and the like are contemplated.

In the novel flame retardant monomer composition, one of the ethylenically unsaturated monomers of a) is covalently bonded directly or through a linking group to the polyphosphate moiety of b), forming a precursor monomer unit. Further, the amine species of c) is in complex, typically a salt, with the covalently bonded polyphosphate moiety of b) in the precursor monomer unit. Thus, although the ethylenically unsaturated monomers of a), the polyphosphate moiety of b) and the amine species of c) are disclosed separately, in the novel flame retardant monomer composition the amine species are present in complex with the polyphosphate moiety, and the polyphosphate moiety is covalently bonded to the ethylenically unsaturated monomers of a).

A flame retardant monomer is one that imparts flame retardancy to a polymer in which it is incorporated.

Example embodiments of the novel flame retardant monomer composition can be, for example, phosphate esters of 2-hydroxyethyl methacrylate complexed with guanyl urea and phosphonic esters of 2-hydroxylethyl methacrylate complexed with guanyl urea. Without wishing to be bound by theory, the novel flame retardant monomer composition may be represented, for example, by the novel flame retardant monomer composition of formula I, as shown in FIG. 1.

In some embodiments of the invention, the term "derived" can mean derived or derivable. In some embodiments, the phosphorus containing monomer can be derived or derivable from (meth)acrylic acid or (meth)acrylamide. By derivable, it is meant that derivation of the monomer is possible from (meth)acrylic acid or (meth)acrylamide, but may also be derived from other materials, such as other (meth)acrylic acid sources, for example, (meth)acrylonitrile in a Ritter reaction. In another example, the (meth)acrylic acid derived flame retardant monomer can be made using a (meth)acrylic acid ester. In such cases as the foregoing examples, the monomer product contains the (meth)acrylic acid or (meth)acrylamide moiety just the same as if it were derived from (meth)acrylic acid or (meth)acrylamide.

As noted above, a precursor monomer unit can be formed from a polyphosphate moiety and an ethylenically unsaturated monomer of a). The polyphosphate moiety can be a polyphosphate or monophosphonate compound of formula $-R_3X-[P(=O)(OR_5)O]_nR_4$, or $-R_3-P(=O)(OR_4)(OR_5)$, where:

X is O or NH, $R_3$ is a $C_0$-$C_{50}$ hydrocarbyl linking group having oxygen and/or nitrogen atoms substituted for up to 20 of the carbon atoms, n can be between about 1 to about 10, or about 1 to about 8, or about 1 to about 6, and preferably from about 1 to about 3, $R_4$ is H, $M^+$, aryl or alkyl, $R_5$ is H, or $M^+$, and $M^+$ is a counterion selected from elements in Groups I and II of the periodic table, or ammonium.

As used herein, ammonium means $NH_4$, or mono-, di-, tri-, or tetra-alkylammonium.

In some embodiments, the polyphosphate moiety can contain a tribasic acid of phosphorus. In some embodiments, the polyphosphate moiety can be derived from carboxyethyl monophosphate, carboxyethyl monophosphonate, carboamidoethyl monophosphate, carboamidoethyl monophosphonate, phenethyl monophosphate, or phenethyl monophosphonate.

Often, the precursor monomer unit, i.e., the unit comprised of the (meth)acrylic acid, (meth)acrylamide, or vinylbenzene covalently bonded to a polyphosphate moiety, may be purchased commercially, but non-commercial precursor monomer units are also contemplated herein. Often commercial precursor monomer units are mixtures, such as, for example, Sipomer™ PAM-4000 available from Rhodia, which is a major part 2-hydroxyethyl (meth)acrylate monophosphate ester (HEMA) and a minor part bis(2-hydroxyethyl (meth)acrylate) phosphate ester. Such mixtures are contemplated herein, as well as precursor monomer units that are pure compositions. HEMA polyphosphate can also be made directly from HEMA and phosphorus pentoxide or phosphoric acid. Alternatively, other monomers such as hydroxypropyl (meth)acrylate or 4-hydroxybutyl (meth)acrylate could be used in place of HEMA. Some other examples of precursor monomer units can include, polyethylene glycol (meth)acrylate phosphate ester (available as PAM-100 from Rhodia), polypropylene glycol (meth)acrylate phosphate ester (available as PAM-200 from Rhodia), methacrylamidoethyl phosphonic acid, vinylbenzene phosphonic acid, vinyl phosphonic acid, and isopropenyl phosphonic acid.

In general, the amine species c) can have a molecular weight of from about 17 to about 3000 g/mole. Suitable amine species for the novel flame retardant monomer composition can be derived from, for example, dicyandiamide, alkylamines, such as, for example, trimethylamine, triethylamine, triethanolamine, and dimethylamine, or guanidine. Other examples of suitable amine compounds are urea, substituted akyl ureas, thiourea, akyl thiourea, cyanamide, ethylenediurea, aniline, ethyleneamines, guanidine, guanamine, benzoguanamine, acetoguanamine, glycoluril, acrylamide, methacrylamide, melamine, benzene sulfonamide, naphthalene sulfonamide, toluene sulfonamide, ammeline, ammelide, guanazole, phenylguanazole, carbamoylguanazole, dihydroxyethyleneurea, ethyleneurea, propylene urea, melem ($C_6H_6N_{10}$), melam ($C_6H_9N_{11}$), octadecylamide, glycine, and their mixtures. A specific example of a suitable amine species for use in the novel flame retardant monomer composition can be guanyl urea, which can be derived from dicyandiamide and water.

Another aspect of the invention is a flame retardant polymer. In one embodiment, the flame retardant polymers may be homopolymers or copolymers comprising the novel flame retardant monomer compositions of the simplest aspect of the invention. In another embodiment, the flame retardant polymers may be a copolymer of A) at least one ethylenically unsaturated monomer unit that is not covalently bonded to a polyphosphate moiety, and B) the novel flame retardant monomer compositions of the simplest aspect of the invention. As a copolymer, the polymer can contain one or more of the same or different ethylenically unsaturated monomer units of A) and/or one or more of the same or different novel flame retardant monomer compositions of B).

In one embodiment, the polymer can include a cross-linking agent. Crosslinking agents can include, for example, phenol derivatives, such as dihydroxybenzenes, including resorcinol, hydroquinone, mono methyl ether hydroquinine, catechol and alkylated dihydroxybenzenes. The cross-linking agent can be present from about 0.1 wt % to about 20 wt % of the polymer, or from 0.5 to about 15 wt %, or 1.0 to about 10.0 wt %.

The addition of a cross-linking agent often improves the ability of the polymer to stay adhered to a surface, such as fibrous filtration media, after being washed by water, in particular non-demineralized water, such as tap-water. In one embodiment, there is provided a method of improving the vertical burn performance of a non-halogen flame retardant polymer after water soaking compared to the polymer without cross-linking, by preparing the polymer with a cross-linking agent. The test for vertical burn is described below in Example 1. In another embodiment, there is provided a method of improving the capacity of a non-halogen flame retardant polymer to withstand tap water washing, comprising preparing the non-halogen flame retardant polymer with a cross-linking agent. In a further embodiment, there is provided a method of maintaining flame retardance on a surface contacted or contactable with water, comprising applying to the surface a polymer composition as discussed herein, including a cross-linking agent.

In some embodiments, the ethylenically unsaturated monomer units of A) can be from 0% or 0.1% of the monomers in the polymer to about 80% of the monomers in the polymer. Likewise, up to about 65% of the monomers in the flame retardant polymer may be ethylenically unsaturated monomer units of A). Alternately, up to about 70% or 75% of the monomers may be the ethylenically unsaturated monomer units of A).

The ethylenically unsaturated monomer units of A) of the present invention can serve, among other things, to provide particular physical characteristics to the polymer. Thus, one of ordinary skill in the art may choose the appropriate ethylenically unsaturated monomer for the flame retardant polymer based on the particular physical characteristics desired for a particular application of the flame retardant polymer.

Some examples of ethylenically unsaturated monomers not covalently bonded to a polyphosphate moiety suitable for use in the flame retardant polymer can be, for example, one or more of, styrene, $C_1$-$C_{40}$ alkyl (meth)acrylates, $C_1$-$C_{40}$ (meth)acrylamides, acrylamide, N-methylolacrylamide (NMA), acrylonitrile, acrylic acid, methacrylic acid, itaconic acid, maleic acid, 2-acrylamido-2-methylpropane sulfonic acid, $C_1$-$C_{40}$ hydroxyalkyl (meth)acrylates, (acetoacetoxy)ethyl methacrylate, $C_1$-$C_{40}$ hydroxyalkyl (meth)acrylamide, diacetone acrylamide, vinyl esters, butadiene, isoprene and dimeric or multi-derivative compounds thereof. In addition, although the flame retardant polymer can be non-halogenated, halogenated ethylenically unsaturated monomers, such as, for example, vinyl chloride, are also contemplated herein as suitable ethylenically unsaturated monomer units of A) in the flame retardant polymers.

In the flame retardant polymer according to the invention, at least 20% of the monomers in the polymer are selected from the novel flame retardant monomer composition. It is also contemplated that up to 100% of the monomers making up the flame retardant polymer can be the novel flame retardant monomer composition. It is also contemplated that at least 30%, at least 40%, or at least 50% of the monomers in the flame retardant polymer can be the novel flame retardant monomer composition. In certain flame retardant polymers according to the invention, at least 35%, at least 45%, and at least 55% of the monomers may be the novel flame retardant monomer composition.

In some embodiments, at least 80%, or at least 85%, or at least 90%, and in some embodiments at least 95% of the monomers in the polymer comprise a combination of the ethylenically unsaturated monomers that are not covalently bonded to a polyphosphate moiety and the novel flame retardant monomer compositions.

Preferably, the flame retardant polymer is comprised of at least 1 wt. % phosphorus and has a number average molecular weight (Mn) of at least about 1000 g/mole. In other embodiments, the flame retardant polymer may contain phosphorus at from about 1 wt. % to about 15 wt. %, or from about 2 wt. % to about 14 wt. %, or from about 5 wt. % to about 10 wt. %. In one embodiment, the flame retardant polymer contains at least 7 wt. % phosphorus and in another the flame retardant polymer contains about, 9 wt. % phosphorus and in another 10.6 wt. % phosphorus.

The Mn of the flame retardant polymer should be at least 1000 g/mole. The Mn can also be from about 50,000 g/mole to about 1,000,000 g/mole, or from about 100,000 g/mole to about 750,000 g/mole. In one embodiment, the Mn of the flame retardant polymer can be about 200,000 g/mole to about 500,000 g/mole.

Surprisingly, the flame retardant polymers comprised of novel flame retardant monomer compositions provide better flame retardant performance than similar polymers that do not include a polyphosphate/amine species.

Process

In a preferred embodiment, the flame retardant polymer may be produced by first producing a mixture of at least one novel flame retardant monomer composition, and subsequently free-radically polymerizing the mixture to form a flame retardant polymer, for example, as shown in formula II.

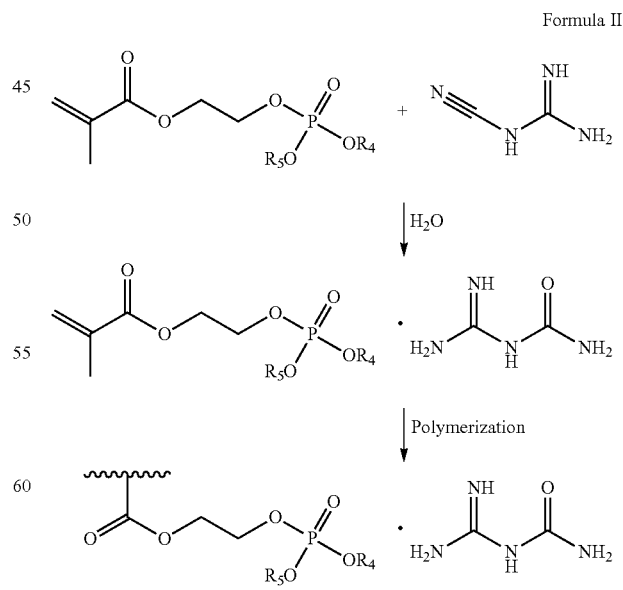

Formula II

In addition, enough ethylenically unsaturated monomer units of A) can be added to the polymerization mixture of the at least one novel flame retardant monomer composition so that the polymerization results in a flame retardant polymer in which 0% to about 80% (or about 0.1 to 75%, or 1 to 65% or 5 to 55%) of the monomers are ethylenically unsaturated monomer units of A) and at least 20% of the monomers are the at least one novel flame retardant monomer composition. By employing the foregoing process, a flame retardant polymer can be produced wherein up to 80%, or up to 85%, or up to 90% of the monomer units in the polymer can be the novel flame retardant monomer composition. Likewise, up to 95% or up to 100% of the monomer units in the polymer can be the novel flame retardant monomer composition.

The mixture of the at least one novel flame retardant monomer composition can be produced, in one embodiment, by reacting a mixture of at least one precursor monomer unit with a mixture of at least one amine species for between 10 minutes and 8 hours, preferably about 1 and 5 hours, at a temperature of between about 20° C. and 100° C., preferably 70° C. to 95° C., to form the mixture of the at least one novel flame retardant monomer composition.

In an alternate embodiment, the flame retardant polymer may be produced by first producing a pre-cursor polymer by free-radically polymerizing precursor monomer units along with enough ethylenically unsaturated monomer units of A) to produce a polymer in which 0% to about 80% of the monomers are ethylenically unsaturated monomer units of A) and at least 20% of the monomers are precursor monomer units. Subsequent to polymerization, the precursor polymer may be reacted with enough amine species to complex the polyphosphate moieties in the precursor monomer units, as shown, for example, in formula III.

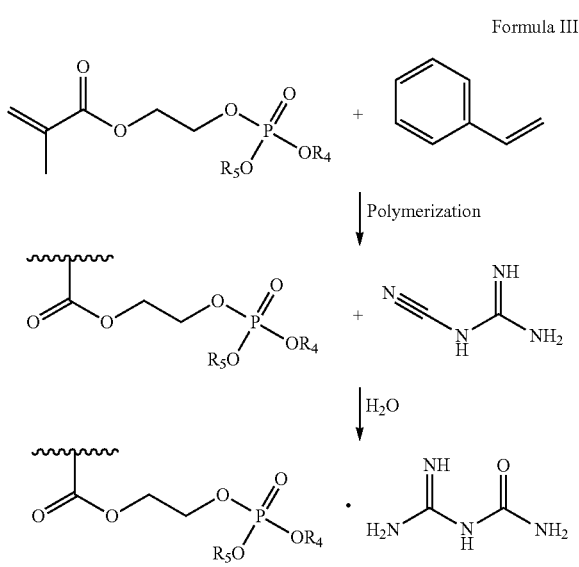

Formula III

By employing the foregoing process, a flame retardant polymer can be produced wherein up to 30%, or up to 35%, or up to 40% of the monomer units in the polymer can be covalently bonded with polyphosphate moieties.

In either process, a cross-linking agent, as discussed above, can be added to the flame retardant composition mixture containing the flame retardant polymer. For example, resorcinol, i.e. dihydroxy benzene, can be added to a completed reaction mixture containing the flame retardant polymer.

Notably, a counterion may be introduced into the compound during pH adjustment. For example, NaOH, KOH, ammonium hydroxide or alkyl ammonium hydroxide may be employed for pH adjustment, resulting in substitution of the hydrogen of one or both of the hydroxyls with a counterion, such as $Na^+$, $K^+$, ammonium, or alkyl ammonium.

In some embodiments, a polymerization catalyst or other standard catalyst may be employed to assist polymerization. Examples of polymerization catalysts can be alkali metal hypophosphite salts, such as sodium hypophosphite, alkali metal phosphites, alkali metal polyphosphates, alkali metal dihydrogen phosphates, polyphosphoric acids, and alkyl phosphinic acids. In the case where a novel flame retardant monomer composition is produced and then polymerized, use of a polymerization catalyst can result in up to 95%, or up to 97.5%, or even up to 100% of the monomer units in the polymer covalently bonded with polyphosphate moieties. Likewise, in the case where polymerization takes place prior to complexing, use of a polymerization catalyst can result in up to 80%, or up to 85%, or up to 88%, or even up to 90% of the monomer units in the polymer covalently bonded with polyphosphate moieties. Solvent can be employed at any point in the processes, including during addition and reaction of the vinyl monomers used in the polymerization.

In either embodiment of the processes to produce the flame retardant polymers, the mixture of the at least one precursor monomer unit can be obtained commercially, or by readily known processes to those of ordinary skill in the art.

In one embodiment the at least one precursor monomer unit can be made directly from the reaction of an alkoxyl (meth)acrylate with phosphorus pentoxide in water.

In the process to produce the flame retardant polymer, the polyphosphate to amine species (P:N) ratio in the amine species reaction step can be from about 1:0.2 to about 1:15. The P:N ratio can also be from about 1:0.5 to about 1:10, or from about 1:1 to about 1:5. Additionally, in either embodiment, the amine species reaction step may be performed in the presence of water. In particular, the reaction step may be completed by reacting the precursor monomer units or precursor polymer with dicyandiamide and water. The reaction with dicyandiamide and water will result in the production of a guanyl urea, which guanyl urea can then complex with the polyphosphate moiety in the precursor monomer units. The complexation reaction may result in other by-products, which by-products are contemplated herein.

In either embodiment, free radical polymerization or copolymerization of the monomers may be by any polymerization process, such as, for example, by dispersion polymerization, solution polymerization, photo-polymerization, or radiation polymerization. Emulsion polymerization may be used. The monomers may be emulsified with an anionic, cationic, or nonionic surfactant or dispersing agent, or compatible mixtures thereof such as a mixture of an anionic and a nonionic surfactant, using, for example, from about 0.05% to about 5% by weight of a surfactant or dispersing agent based on the weight of the monomer. Suitable cationic dispersion agents include lauryl pyridinium chloride, cetyldimethyl amine acetate, and alkyldimethylbenzylammonium chloride, in which the alkyl group has from 8 to 18 carbon atoms. Suitable anionic dispersing agents include, for example, alkali fatty alcohol sulfates, such as sodium lauryl sulfate, and the like; arylalkyl sulfonates, such as potassium isopropylbenzene sulfonate, and the like; alkali alkyl sulfosuccinates, such as sodium octyl sulfosuccinate, and the like; and alkali arylalkylpolyethoxyethanol sulfates or sulfonates, such as sodium t-octylphenoxypolyethoxyethyl sulfate, having 1 to 5 oxyethylene units, and the like. Suitable non-ionic dispersing agents include, for example, alkyl phenoxypolyethoxy ethanols having alkyl groups of from about 7 to 18 carbon atoms and from about 6 to about 60 oxyethylene units such as, for example, heptyl phenoxypolyethoxyethanols; ethylene oxide derivatives of long chained carboxylic acids such as lauric acid, myristic acid, palmitic acid, oleic acid, and the like, or mixtures of acids such as those found in tall oil containing from 6 to 60 oxyethylene units; ethylene oxide condensates of long chained alcohols such as octyl, decyl, lauryl, or cetyl alcohols containing from 6 to 60 oxyethylene units; ethylene oxide condensates of long-chain or branched chain amines such as dodecyl amine, hexadecyl amine, and octadecyl amine, containing from 6 to 60 oxyethylene units; and block copolymers of ethylene oxide sections combined with one or more hydrophobic propylene oxide sections. High molecular weight polymers such as hydroxyethyl cellulose, methyl cellulose, polyacrylic acid, polyvinyl alcohol, and the like, may be used as emulsion stabilizers and protective colloids. Alternatively, the monomers can be polymerized without a surfactant.

The polymerization may be initiated in the presence of a small particle size preformed emulsion polymer (e.g., seed polymerization), or unseeded. Seeded polymerization may yield an aqueous dispersion of latex polymer having more uniform particle size than unseeded polymerization.

Chain transfer agents may be used to control molecular weight and include mercaptans, polymercaptans, alcohols, and halogen compounds used in the polymerization mixture in order to moderate the molecular weight of the polymeric binder. Generally, from 0% to about 3% by weight, based on the weight of the polymeric binder, of $C_4$-$C_{20}$ alkyl mercaptans, mercaptopropionic acid, or esters of mercaptopropionic acid, may be used.

The polymerization process may comprise a batch process, continuous process, staged process, or a process involving any other method. Each stage of a staged process may incorporate thermal or redox initiation of polymerization. A monomer emulsion containing all or some portion of the monomers to be polymerized in a given stage may be prepared using the monomers, water, and emulsifiers. A solution of initiator in water may be separately prepared. The monomer emulsion and initiator solution may be co-fed into the polymerization vessel over the course of the emulsion polymerization of any stage of the process. The reaction vessel itself may also initially contain seed emulsion and further may additionally contain an initial charge of polymerization initiator. The temperature of the contents of the reaction vessel may be controlled by cooling to remove heat generated by the polymerization reaction or by heating the reaction vessel. Several monomer emulsions may be simultaneously co-fed into the reaction vessel. When multiple monomer emulsions are co-fed, they may be of different novel flame retardant monomer composition. The sequence and rates at which the monomer emulsions are co-fed may be altered during the emulsion polymerization process. After addition of the first monomer emulsion(s) has been completed, the polymerization reaction mixture may be held at some temperature for a time and/or treated with a polymerization inhibitor prior to polymerization of the subsequent monomer emulsion(s). Similarly, after addition of the final monomer emulsion(s) has been completed, the polymerization reaction mixture may be held at some temperature for a time and/or treated with a polymerization inhibitor before cooling to ambient temperature.

The pH of the polymers can be adjusted to about 3.0 to about 10.0 in the premix or in the emulsion polymer with commonly used base, such as, for example, ammonium hydroxide, sodium or potassium hydroxide, magnesium hydroxide, tri(m)ethylamine and the like.

Flame Retardant Compositions

The flame retardant polymers may contain conventional ingredients such as solvents, plasticizers, pigments, dyes, fillers, emulsifiers, surfactants, thickeners, rheology modifiers, heat and radiation stabilization additives, defoamers, leveling agents, anti-cratering agents, fillers, sedimentation inhibitors, U.V. absorbers, antioxidants, flame retardants, etc. It may contain other polymeric species such as additional polymers in the forms of blends, interpenetrating networks, etc.

In one embodiment, the flame retardant polymers may be blended with additional flame retardant additives, which are well known in the literature and art. Exemplary flame retardant additives include non-halogen flame retardants, such as melamine and melamine derivatives, such as melamine cyanurate, melamine borate, melamine phosphate, melamine molybdate; borates; organic phosphates, organic phosphinates such as, for example, Exolit™ OP 1230 and 1311 available from Clariant, and phosphorus containing compounds, such as, 9,10-dihydro-9-oxa-10-phosphaphenanthrene-10-oxide, tetrakis(hydroxymethyl)phosphonium chloride and bis[tetrakis(hydroxymethyl)phosphonium]sulfate; inorganic compounds such as aluminum trihydrate, antimony oxide, ammonium phosphate, ammonium polyphosphate, calcium carbonate, clay, and talc. Although, in some embodiments, the flame retardant polymers are desired to be non-halogenated, blending the flame retardant polymers with halogenated flame retardants, such as chlorinated and brominated compounds, such as pentabromodiphenyl ether, octabromodiphenyl ether, decabromodiphenyl ether, and hexabromocyclododecane, is contemplated herein. Often more than one flame retardant is used and frequently 3 or more flame retardants are combined in flame retardant formulations. The level of flame retardants used in conjunction with the flame retardant polymers and copolymers of the present invention can be from about 1 to about 50 parts by weight of flame retardant additive per 100 parts by weight of the flame retardant polymer.

Just as the ethylenically unsaturated monomers can be chosen to impart particular physical properties to the flame retardant polymer, additional polymers can be blended with the flame retardant polymers and copolymers of the present invention to produce blends of further flame retardancy or with certain physical properties. Examples of other polymers that may be blended can include polyurethane polymers, polyamide polymers, polyurea polymers, polyester polymers, polyacrylate polymers, phenolic resins or mixtures thereof.

The polymer may be combined with other commercial polymers or polymer dispersions by methods known to those skilled in the art. The polymer may be used for forming hybrids with other polymers such as urethanes or silicones. This may be done by polymerizing additional monomers by emulsion or suspension polymerization in the presence of the polymer, blending the polymer with other preformed polymers, or synthesizing the polymer in the presence of other polymers.

In one embodiment, the polymer may be mixed with a phenolic resin in a condensation reaction, preferably containing 0.5-10 wt. % of N-methylol (meth)acrylamide (NMA).

Adjuvants useful in the preparation of the polymer and/or in its subsequent use may be added during or subsequent to the polymerization reaction. These may include auxiliary surfactants; defoamers such as, for example, SURFYNOL™ 104E and Nopco™ NXZ used at a level from about 0.001 to about 0.1 wt. % based on the weight of the monomer mixture; leveling agents such as, for example, Sag™ Silicone Antifoam 47, used at a level from about 0.001 to about 0.1 wt. % based on the weight of the monomer mixture; antioxidants such as, for example, MAROXOL™ 20 and IRGANOX™ 1010 used at a level from about 0.1 to about 5 wt. % based on the weight of the monomer mixture; plasticizers such as, for example, FLEXOL™ plasticizer; and preservatives such as, for example, KATHON™ at a level of about 30 to about 45 parts per million (ppm), or PROXEL™ GXL at a level of about 300 to about 500 ppm.

Flame Retardant Applications

In one embodiment, the flame retardant compositions described above can be employed as a coating for fibrous filtration media. Use of the flame retardant compositions have exhibited a particular advantage in fibrous filter media by improving flame retardancy without negatively effecting the air permeability or pressure drop through the fibrous filter. That is, fibrous filter media coated with the novel flame retardant compositions have improved air permeability and exhibit lower pressure drops than prior art flame retardant compositions.

Fibrous filtration media can include a) filtration fabric also known as "paper" or rolled goods; b) synthetic filtration fabrics often referred to as "non-wovens" such as polypropylene, polyethylene, polystyrene, and related polyolefins; fiberglass; glass microfibers; polyamides such as nylon (6 and 6/6), Kevlar, Nomex; polyesters such as Dacron; polyacrylates, polymethacylates, polyacryonitrile such as Orion, polyvinyl chlorides and related materials, such as Saran; polytetrafluoroethylene; polyurethanes; copolymers of the above materials; and combinations thereof; c) natural filtration fabric such as cellulose and other paper-based filtration media paper; wool; cotton; hemp; fiber glass; glass microfibers, carbon fibers; and combinations thereof; and d) Woven fabric made from fibers such as cotton, nylon 6, polytetrafluorethylene (PTFE), nylon 6.6, nylon 11, nylon 12, halar (E-CTFE), polyester PBT, Polyester PET, polypropylene, acrylics, polyvinyl-den fluoride (PVDF), polyphosphate sulfide (PPS) and high density polyethylene, (e) filter aids such as adsorbents like diatomaceous earth, perlite, activated carbon, carbon black and related materials, anthracite, silicas, aluminas, and combinations thereof. Combinations of filter media can be used.

The types of filters that can be coated with the coating composition include filter pads, filter bags, filter cartridges, pleated filters, membrane filters, strainers, screens, candle filters, plastic filters, ceramic filters, filter presses, belt filters, rotary drum filters, leaf filters, plate filters, disc filters, "precoat filters", a filter bed on a strainer element or support, air filters, and the like.

The coated filters can be useful for the filtration of gases for the removal of solid contaminants which are exemplified by dirt particles, dust, $SiO_2$, $Al_2O_3$, $Fe_2O_3$, CaO, MgO, $Na_2O$, $K_2O$, $TiO_2$, clays, solid metal particles, carbon materials such as carbon black and activated carbon, particulates in industry, and combinations thereof, removal of odors, removal of toxic materials, and the filtration of other gases such as nitrogen, oxygen, carbon dioxide and the like, or flue gases, residual Hg, $SO_3$ and the like and combinations thereof and the filtration of aerosols, removal of acids (HIC, acetic acid, etc.). The filters may be antibacterial and antiviral.

The coated filter can be useful for the filtration of liquids for the removal of water-insoluble contaminants such as solids contaminants which are exemplified by dirt particles, dust, $SiO_2$, $Al_2O_3$, $Fe_2O_3$, CaO, MgO, $Na_2O$, $K_2O$, $TiO_2$, clays, solid metal particles, carbon materials such as carbon black and activated carbon, particulates in industry, and combinations thereof. The coated filter is useful for the removal of liquid contaminants such as insoluble and non-miscible liquids such as aromatic compounds, hydrocarbons, halocarbons and combinations thereof. The coated filter is also useful for the removal of water-soluble contaminants such as water-soluble metal ions and metal oxides such as Hg, Cu, $H_3AsO_3$, $H_3AsO_4$, Pb, Cd, Ba, Be, Se, and the like; acids such as carboxylic acids, inorganic acids such as sulfuric acid), bases such as metal hydroxides, metal bicarbonates and carbonates; amines; soluble chemical contaminants such as amines, sulfur compounds, phosphorus compounds, unsaturated compounds, phenols, MTBE (methyl t-butyl ether), chlorocarbons (and other halocarbons); aromatic compounds such as phenols, alcohols, and the like; gases such as $CO_2$, $SO_2$, $H_2S$; odorous materials and combinations thereof. Furthermore, the coated filter on a filtration media is useful for the removal of fluid-insoluble particles contaminants such as by dirt ($SiO_2$, etc.); wear debris in engines and machinery; as CaO particulates in the manufacture of detergents; carbon black and activated carbon in manufacturing such as in the pharmaceutical industry; soot and other carbon-based solids in engine oils and combinations thereof.

The flame retardant polymers can be added to fibrous filter media by any conventional means, for example, by impregnation, saturation, foam coating, spraying, dipping or other coating procedure after preparing a thread, woven cloth, or nonwoven fabric from fibers, or kneading or blending with a synthetic polymer fiber in melting, extruding and spinning processes. A method of introducing a flame retardant by chemical bonding, such as covalent bonding in preparing polymer may also be employed.

The flame retardant compositions described herein exhibit advantages over prior art compositions employed as coatings on fibrous filter media. The coatings can provide flame retardancy at lower pickup levels than some prior art fibrous filter coatings. Fibrous filter coatings of the flame retardant compositions do not significantly affect filtration efficiency, noticeably increase pressure, or decrease flow rate through the filter. Moreover, the compositions are not easily removed by water, as exemplified below where the coating composition maintains flame retardancy even after the filter upon which the composition is coated is repeatedly washed with water.

It is known that some of the materials described above may interact in the final formulation, so that the components of the final formulation may be different from those that are initially added. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

Sample 1—Flame Retardant ("FR") Polymer with Resorcinol

HEMA (272.48 g, 2.10 mole) and butylated hydroxytoluene (BHT) (0.16 g) are placed in a 1 liter 3-neck reactor. Phosphorous pentoxide (148.82 g, 1.05 mole) is added in portions under air to keep the temperature below 60° C. The reaction is then heated under air with an oil bath to 60° C. for 2 hours. The oil bath is removed and demineralized ("DM") water (20 g, 1.2 mole) is added slowly to keep temperature below 60° C. The mixture is heated at 60° C. for one more hour. The oil bath is removed and dicyandiamide (176.06 g, 2.10 mole) is added in portions to keep temperature below 70° C., followed by DM water (44 g, 2.44 mole). After the exotherm subsides, the reaction is heated under air to 90° C. for 3 hours before cooling down to 60° C. 320 g DM water is then added to make an aqueous solution.

A mixture of 400 g of the solution prepared as described above, 114 g styrene, 52 g 2-ethylhexylacrylate and 28 g NMA was adjusted to pH 4.2 with 6.24 g 28% ammonium hydroxide and rinsed with 20 g DM water to obtain a premix. 700 g DM water is heated to 75° C. under nitrogen atmosphere and 2 g ammonium persulfate (APS) in 20 g water is added in one shot. When the temperature returns to 75° C., the aforementioned premix is metered in over 80 minutes, then flushed with 20 g water. 30 minutes later, 0.4 g APS in 8 g water was added and the polymerization continued for 30 more minutes before cooling to 57° C. A redox initiator of 1.2 g 70% t-butyl hydroperoxide (t-BHP) in 10 g DM water is added followed by 0.64 g Bruggolite FF-6 in 12 g water. The mixture is stirred at 57° C. for 60 min. A second redox initiator of 0.6 g tBHP in 5 g water followed by 0.32 g FF-6 in 6 g water. The mixture is allowed to cool while stirring. 1.5 g resorcinol was added and stirred for 30 minutes at room temperature. The pH of the latex is 4.4.

Comparative 1—FR Polymer with 70% of Monomers being PAM-4000 in Complex with Guanyl Urea 300 g Sipomer™ PAM-4000, 120 g dicyandiamide, 0.3 g BHT and 420 g water are reacted at 90° C. for 2 hours. The product is mixed with 12 g of 48% NMA and 128.6 g ethyl acrylate (EA) to be pumped in 3 hours into a reactor containing 775 g water and 60 g dicyandiamide initiated with 2.4 g APS in 25 g water at 75° C., as described in previous examples. 12 g water is used to flush the line. Additional 0.45 g APS in 12 g water is added 30 minutes later. The mixture is stirred for 30 minutes before cooling to 62° C. The mixture is redoxed twice with 0.31 g APS in 12 g water and 0.31 g FF-6 in 20 g water before cooling down. The product is filtered through a double layered cheese cloth with no apparent coagulum.

Example 1—Control Vertical Burn Performance Data

Paper impregnated with a control composition of Hycar™ latex, which is a commercial latex composition available from The Lubrizol™ Corporation, is tested for flame retardancy. The control composition is also tested with commercial flame retardant additives. PAM-4000 is also tested on its own as a cast film dried at ambient temperature and cured at 300° F. for 5 minutes. The controls are tested in a vertical burn test according to TAPPI 461, Apparatus 3.1 to 3.4, both before water soaking and after being soaked in demineralized water for 24 hours and dried. Results are shown in Table 1.

TABLE 1

| | | FLAME RETARDENCY VERTICAL Burn | | | |
| | | Before water soaking | | After water soaking | |
| Polymer | % Binder Content | 1st | 2nd | 1st | 2nd |
|---|---|---|---|---|---|
| PAM-4000 | N/A | CB | CB | n/a | n/a |
| Hycar 26846 | 20.2-20.7 | CB | CB | CB | CB |
| 100 parts Hycar 26846 + 100 parts Pyrosan SYN | 34.7 | SE | SE | CB | CB |
| 100 parts Hycar 26846 + 100 parts NH$_4$Sulfomate | 34.7 | SE | CB | CB | CB |
| 100 parts Hycar 26846 + 100 parts Antiblaze LR3 | 33.9 | SE | SE | CB | CB |
| 100 parts Hycar 26846 + 100 parts Antiblaze LR4 | 32.9 | SE | SE | CB | CB |
| 100 parts Hycar 26846 + 100 parts Antiblaze MC | 33.4 | SE | SE | CB | CB |
| 100 parts Hycar 26846 + 100 parts Martinal OL-104 LE | 32.4 | CB | CB | CB | CB |
| 100 parts Hycar 26846 + 100 parts Melapur MP | 32.0 | SE | SE | CB | CB |

"SE" means self-extinguished and "CB" means complete burn.
Pyrosan ™ SYN is an organic phosphate compound available from Emerald Performance Materials.
Antiblaze ™ LR3, LR4, and MC are ammonium polyphosphates available from Albemarle Corp.
Martinal ™ OL-104 LE is an aluminum hydroxide available from Albemarle Corp.
Melapur ™ MP is a melamine phosphate available from DSM Melapur.

Example 2—Sample Vertical Burn Performance Data

Paper impregnated with Sample 1 and Comparative 1, are tested for flame retardancy. The compositions are tested in a vertical burn test according to TAPPI 461, Apparatus 3.1 to 3.4, both before water soaking and after being soaked in demineralized water and tap water. In each case, soaking was for an initial 2 hours, after which the sample was removed and the water bath was changed with fresh water and another soaking occurred for 2 more hours. Again, after the second 2 hours the bath was changed again with fresh water and another 2 hour soak occurred. After the third 2 hour soak (6 hours total soak), the paper was dried and tested for vertical burn. Soaking in tap water provides a more vigorous test of post water soaking performance. Results are shown in Table 2.

TABLE 2

| | % Binder Content | Vertical Burn | | |
| | | Before Soaking | After DM Water Soaking | After Tap Water Soaking |
| --- | --- | --- | --- | --- |
| Comparative 1 | 31.2 | SE | SE | CB |
| Sample 1 | 31.4 | SE | SE | SE |

Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A flame retardant monomer composition comprising:
   a) a group derived from one of a (meth)acrylic acid, (meth)acrylamide, or vinylbenzene,
   b) a polyphosphate moiety,
   c) guanyl urea, and
   d) a cross-linking agent that is resorcinol, catechol, alkylated dihydroxybenzene, or mixtures thereof;
   wherein a) is covalently bonded directly or through a linking group to b) forming a precursor monomer unit, and
   wherein c) is in complex with the covalently bonded polyphosphate moiety of b) in the precursor monomer unit.

2. The composition of claim 1 wherein the polyphosphate moiety is derived from a polyphosphate or monophosphonate compound of formula $-R_3X-[P(=O)(OR_5)O^-]_nR_4$, or $-R_3-P(=O)(OR_4)(OR_5)$, where:
   n is about 1 to about 10
   X is O or NH,
   $R_3$ is a $C_0$-$C_{50}$ hydrocarbyl linking group having oxygen and/or nitrogen atoms substitute for up to 20 of the carbon atoms,
   $R_4$ is H, or $M^+$,
   $R_5$ is H, or $M^+$, and
   $M^+$ is a counterion selected from elements in Groups I and II of the periodic table or ammonium.

3. The composition according to claim 1 wherein the polyphosphate moiety is carboxyethyl monophosphate, carboxyethyl monophosphonate, carboamidoethyl monophosphate, carboamidoethyl monophosphonate, phenethyl monophosphate, or phenethyl monophosphonate, or mixtures thereof.

4. A composition according to claim 1, wherein the precursor monomer unit is selected from 2-hydroxyethyl (meth)acrylate monophosphate ester, bis(2-hydroxyethyl (meth)acrylate diphosphate ester, polyethylene glycol (meth)acrylate monophosphate ester, polypropylene glycol (meth)acrylate monophosphate ester, methacrylamidoethyl phosphonic acid, vinylbenzene phosphonic acid, vinyl phosphonic acid, and isopropenyl phosphonic acid.

5. The composition according to claim 1 wherein the amine species has a molecular weight of from about 16 to 3000 g/mole.

6. The composition according to claim 1 wherein the amine species is derived from dicyandiamide, an alkylamine, or guanidine.

7. A composition according to claim 1 wherein the flame retardant monomer composition is 2-(phosphonooxy)ethyl methacrylate complexed with guanyl urea or (2-(methacryloyloxy)ethyl)phosphonic acid complexed with guanyl urea.

8. A flame retardant polymer comprised of monomeric units equivalent to a flame retardant monomer composition comprising: (a) a group derived from at least one of (meth)acrylic acid, (meth)acrylamide, or vinylbenzene, (b) a polyphosphate moiety, and (c) guanyl urea, wherein (a) is covalently bonded directly or through a linking group to b), forming a precursor monomer unit, and wherein (c) is in complex with the covalently bonded polyphosphate moiety of (b) in the precursor monomer unit, and wherein the flame retardant polymer is crosslinked with resorcinol, catechol, alkylated dihydroxybenzene, or mixtures thereof.

9. The flame retardant polymer of claim 8, wherein the flame retardant polymer is a homopolymer.

10. The flame retardant polymer according to claim 8, additionally comprising ethylenically unsaturated monomers that are not covalently bonded to a polyphosphate moiety.

11. The flame retardant polymer of claim 10, wherein at least 20% of the flame retardant polymer is comprised of the flame retardant monomer compositions and from 0.1% to about 80% of the flame retardant polymer is comprised of the ethylenically unsaturated monomers that are not covalently bonded to a polyphosphate moiety, and wherein the flame retardant polymer is comprised of at least 1 wt. % P and has a Mn of at least about 1000 g/mole; and wherein at least 90% of the flame retardant polymer comprises a combination of the ethylenically unsaturated monomers that are not covalently bonded to a polyphosphate moiety and the flame retardant monomer compositions, wherein said ethylenically unsaturated monomers that are not covalently bonded to a polyphosphate moiety are one or more of vinyl chloride, styrene, $C_1$-$C_{40}$ alkyl (meth)acrylates, $C_1$-$C_{40}$ (meth)acrylamides, acrylamide, N-methylolacrylamide (NMA), acrylonitrile, acrylic acid, methacrylic acid, itaconic acid, maleic acid, 2-acrylamido-2-methylpropane sulfonic acid, $C_1$-$C_{40}$ hydroxyalkyl (meth)acrylates, $C_1$-$C_{40}$ hydroxyalkyl (meth)acrylamide, vinyl esters, butadiene, isoprene and derivatives thereof.

12. The flame retardant polymer according to claim 8 wherein the phosphorus content is from about 1.0 to about 15.0 wt. % of the flame retardant polymer.

13. A method of maintaining flame retardance on a surface contacted or contactable with water, comprising applying to the surface a polymer composition as claimed in claim 8.

14. A composition comprising the flame retardant polymer according to claim 8, and further comprising from about 1 to about 50 parts by weight of a flame retardant additive per 100 parts by weight of said flame retardant polymer.

15. The composition of claim 14, wherein the flame retardant additive is one or more of a melamine derivative flame retardant, an organic flame retardant, an inorganic flame retardant, an organic phosphate, phosphonate or phosphinate flame retardant, a halogenated compound flame retardant, and mixtures thereof.

16. The composition of claim 15, wherein the flame retardant additive is melamine cyanurate.

17. The composition of claim 14 additionally blended with one or more polyurethane polymers, polyamide polymers, polyurea polymers, polyacrylate polymers or mixtures thereof.

* * * * *